(12) United States Patent
Douroumis et al.

(10) Patent No.: US 10,543,638 B2
(45) Date of Patent: Jan. 28, 2020

(54) STENT

(71) Applicant: The University of Greenwich, London (GB)

(72) Inventors: Dionysios Douroumis, Kent (GB);
Michael S. A. Bradley, Kent (GB);
Nicolaos Scoutaris, Kent (GB)

(73) Assignee: The University of Greenwich, London (GB)

( * ) Notice: Subject to any disclaimer, the term of this patent is extended or adjusted under 35 U.S.C. 154(b) by 97 days.

(21) Appl. No.: 15/545,572

(22) PCT Filed: Jan. 20, 2016

(86) PCT No.: PCT/GB2016/050119
§ 371 (c)(1),
(2) Date: Jul. 21, 2017

(87) PCT Pub. No.: WO2016/116748
PCT Pub. Date: Jul. 28, 2016

(65) Prior Publication Data
US 2018/0229426 A1    Aug. 16, 2018

(30) Foreign Application Priority Data

Jan. 22, 2015 (GB) .................................. 1501089.5

(51) Int. Cl.
*A61F 2/06* (2013.01)
*B29C 64/112* (2017.01)
(Continued)

(52) U.S. Cl.
CPC .............. *B29C 64/112* (2017.08); *A61F 2/90* (2013.01); *A61F 2/91* (2013.01); *A61F 2/915* (2013.01);
(Continued)

(58) Field of Classification Search
CPC ..................................... A61F 2/07; A61F 2/89
(Continued)

(56) References Cited

U.S. PATENT DOCUMENTS 6,942,830 B2 * 9/2005 Mulhaupt ............. B29C 31/045
264/255
7,625,198 B2 * 12/2009 Lipson .................... A61L 27/36
425/174

(Continued)

FOREIGN PATENT DOCUMENTS

CN       103815992 A    5/2014
DE    202012009561 U1   11/2012
(Continued)

OTHER PUBLICATIONS

GB Application No. 1501089.5 UKIPO Search Report dated May 15, 2015, 6 pages.
(Continued)

*Primary Examiner* — Suzette J Gherbi
(74) *Attorney, Agent, or Firm* — Linda B. Huber; Nixon Peabody LLP (57) ABSTRACT

The invention provides a method of manufacturing a stent (12) using a three dimensional (3D) printer. The invention also extends to 3D printed stents and second medical uses of such stents. The invention also extends to electric signals carrying computer-executable instructions adapted to cause a 3D printer to print a stent, computer-readable programs and computer-readable mediums.

21 Claims, 7 Drawing Sheets

(51) Int. Cl.
*A61F 2/90* (2013.01)
*A61F 2/91* (2013.01)
*A61F 2/915* (2013.01)
*B33Y 80/00* (2015.01)
*B33Y 10/00* (2015.01)
*B33Y 30/00* (2015.01)
*B33Y 40/00* (2015.01)
*B33Y 50/02* (2015.01)
*B29C 64/188* (2017.01)
*B29C 64/209* (2017.01)
*B29C 64/393* (2017.01)
*A61L 31/06* (2006.01)
*A61L 31/14* (2006.01)
*A61L 31/16* (2006.01)
*B29K 91/00* (2006.01)
*B29K 101/12* (2006.01)
*B29K 105/00* (2006.01)
*B29L 31/00* (2006.01)

(52) U.S. Cl.
CPC ............. *A61L 31/06* (2013.01); *A61L 31/148* (2013.01); *A61L 31/16* (2013.01); *B29C 64/188* (2017.08); *B29C 64/209* (2017.08); *B29C 64/393* (2017.08); *B33Y 10/00* (2014.12); *B33Y 30/00* (2014.12); *B33Y 40/00* (2014.12); *B33Y 50/02* (2014.12); *B33Y 80/00* (2014.12); *A61F 2210/0004* (2013.01); *A61F 2240/001* (2013.01); *A61F 2250/0067* (2013.01); *B29K 2091/00* (2013.01); *B29K 2101/12* (2013.01); *B29K 2105/0035* (2013.01); *B29K 2105/0097* (2013.01); *B29K 2995/0056* (2013.01); *B29K 2995/0077* (2013.01); *B29K 2995/0097* (2013.01); *B29L 2031/7534* (2013.01)

(58) Field of Classification Search
USPC .................................................. 623/1.15–1.48
See application file for complete search history.

(56) References Cited

U.S. PATENT DOCUMENTS

| | | | |
|---|---|---|---|
| 8,691,274 B2* | 4/2014 | Xu ........................ | A61L 27/50 347/1 |
| 2005/0015046 A1 | 1/2005 | Weber et al. | |
| 2009/0208577 A1* | 8/2009 | Xu ........................ | A61L 27/38 424/484 |
| 2015/0306282 A1* | 10/2015 | Scanlon ................. | A61L 31/14 623/1.11 |
| 2015/0374450 A1* | 12/2015 | Mansfield ............. | B29C 64/165 264/219 |
| 2016/0235504 A1* | 8/2016 | Siegmund ......... | A61C 13/0004 |
| 2017/0218228 A1* | 8/2017 | Jose ........................ | C09D 11/03 |
| 2017/0355132 A1* | 12/2017 | Moore ................. | B29C 41/02 |
| 2018/0117219 A1* | 5/2018 | Yang ..................... | B29C 41/00 |
| 2018/0360628 A1* | 12/2018 | Yan ......................... | A61F 2/89 |
| 2018/0370141 A1* | 12/2018 | Eller ..................... | B33Y 10/00 |
| 2019/0000628 A1* | 1/2019 | Hollister ................. | A61F 2/28 |
| 2019/0008998 A1* | 1/2019 | Cui ........................ | A61L 27/16 |
| 2019/0031911 A1* | 1/2019 | Rolland ............... | C09D 175/04 |

FOREIGN PATENT DOCUMENTS

| | | |
|---|---|---|
| WO | 2007045000 A2 | 4/2007 |
| WO | 2014126834 A2 | 8/2014 |
| WO | 2014158460 A1 | 10/2014 |
| WO | 2015023077 A1 | 2/2015 |
| WO | 2016116748 A1 | 7/2016 |

OTHER PUBLICATIONS

International Search Report and Written Opinion for PCT/GB2016/050119 dated Apr. 5, 2016, 12 pages.

Melgoza et al., Rapid Tooling Using 3D Printing System for Manufacturing of Customized Tracheal Stent, Rapid Prototyping Journal, 2014, vol. 20(1), pp. 2-12.

* cited by examiner

STENT

CROSS-REFERENCE TO RELATED APPLICATIONS

This application is a National Phase of International Application No. PCT/GB2016/050119 filed Jan. 20, 2016, currently pending, which designated the U.S. and that International Application was published under PCT Article 21(2) in English. This application also includes a claim of priority under 35 U.S.C. § 119(a) and § 365(b) to British patent application No. GB 1501089.5 filed Jan. 22, 2015, the entirety of which is hereby incorporated by reference.

The invention relates to stents, and to novel methods of manufacturing stents using three dimensional (3D) printing. The invention also extends to stents created using the methods according to the invention, in particular bioabsorbable and drug-eluting stents. The invention extends to the use of printer nozzles to print 3D stents and computer readable mediums used to print 3D stents.

A stent is a tubular mesh, which is designed to prevent or reduce a localized reduction in vascular blood flow caused by stenosis. This is achieved by insertion of the stent into the lumen of the blood vessel. A catheter is used to introduce the stent into the stenotic blood vessel. Once in position, a balloon inside the lumen of the stent is inflated in order to cause the stent to expand and brace itself against the inner wall of the stenotic blood vessel.

Stents were originally made out of or coated with metals such as stainless steel, nitinol, tantalum, platinum or cobalt alloys. However, although metal stents are capable of preventing or reducing stenosis due to their strength and rigidity, they are not biocompatible. Consequently, in recent years, new generation stents, which are biocompatible, have been created. These stents are made out of polymeric materials, such as poly-lactic acid (PLA). Use of biocompatible polymeric materials has also resulted in the manufacture of bioabsorbable and drug-eluting stents.

Bioabsorbable stents provide support for arterial walls but only during the healing process. The mechanical load placed on these stents is gradually transferred back to the surrounding vascular tissue as the mass and strength of the stent decrease due to absorption over time. After the stent has been completely absorbed, it leaves behind a non-stenotic blood vessel. The absence of any stenosis, as well as the stent, mean that late stent thrombosis is less likely to occur. Thus, the need for prolonged antiplatelet therapy is negated. Bioabsorbable stents are suitable for complex anatomy where stents impede vessel geometry and morphology and are prone to crushing and fractures, such as is seen in saphenous femoral and tibial arteries. They also improve the lesion imaging with computed tomography or magnetic resonance.

Drug-eluting stents are currently created by spraying the desired drug on to the surface of a stent using an atomizing nozzle or dip-coating the stent in a bath filled with the drug. Although drug-eluting stents have led to a significant reduction in the rate of restenosis, they are still associated with subacute and late thrombosis, and necessitate prolonged antiplatelet therapy for at least 12 months. Furthermore, polymers used as a vehicle for drug delivery irritate blood vessels and cause endothelial dysfunction, vessel hypersensitivity and chronic inflammation at the site of the stent. In addition, known methods of creating stents tend to lead to a mismatch between the diameter of the stent and the lumen of the vessel into which the stent is to be inserted. This is partly to do with the limitation of modern imaging technologies, such as magnetic resonance imaging (MRI) and multislice computerized tomography (MSCT), which are used to determine the size of a blood vessel's lumen.

Although newer generation stents are no longer made out of or coated with metallic materials, laser cutting technology is still considered the mainstay with respect to stent manufacture. A laser cutter is used to cut and remove material from the wall of a cylinder in order to convert the cylinder into a stent. Unfortunately, the material that has been removed is not re-used. Therefore, a large amount of the source material is wasted. In addition, it has also been found that it is difficult to achieve the appropriate mechanical strength when using laser cutting technology due to the struts of the stent being too thin, too thick or not being spaced apart correctly.

There is therefore a need for an improved method of creating biocompatible stents.

It is believed that three dimensional (3D) printing may provide a solution to the problems that are associated with using laser cutting technology to manufacture stents. Consequently, the inventors decided to experiment with 3D printing. After overcoming various technical problems, they found that it is possible to print 3D biocompatible stents.

Thus, in a first aspect of the invention, there is provided a method of manufacturing a stent using a three dimensional (3D) printer, the method comprising:
  (i) installing a computer-readable design of a stent on a computer, which is operably connected to a 3D printer comprising a nozzle; and
  (ii) instructing the 3D printer to print the design of the stent, such that non-metallic ink is expelled from the nozzle to thereby form the stent.

3D printing, also known as additive manufacturing, involves laminating a plurality of layers to create a 3D object. Unlike laser cutting, excision or removal of material from the source material is not required. Advantageously, therefore, there is minimal wastage of the source material, which is used to print the 3D object.

As a result of their studies, the inventors surprisingly found that a variety of factors influence the ability of a 3D printer to print a stent, one such factor being the diameter of the printer nozzle's outlet aperture.

Hence, the diameter of the printer nozzle outlet aperture may be at least 10 µm, 25 µm or 50 µm. Preferably, the diameter of the printer nozzle's outlet aperture is at least 75 µm, 85 µm or 100 µm. Preferably, the diameter of the printer nozzle's outlet aperture is less than 600 µm, 500 µm or 450 µm. Preferably, the diameter of the printer nozzle's outlet aperture is less than 400 µm, 350 µm or 300 µm. It will be appreciated that any combination of the upper and lower values for the diameter of the outlet aperture of the printer nozzle are possible. For example, preferably the diameter of the printer nozzle's outlet aperture is 10 µm to 600 µm, more preferably 25 µm to 500 µm, and even more preferably 50 µm to 450 µm. Preferably, the diameter of the aperture of the printer nozzle is 75 µm to 400 µm, still more preferably 85 µm to 350 µm, and most preferably 100 µm to 300 µm.

The stent may be printed on a stage. The inventors also found that the printer resolution and the accuracy with which the stage and the nozzle move in the x-, y- and z- planes are also important factors. The resolution of a 3D printer refers to the thickness of each layer of the stent produced using the method according to the invention. In order to print the stent, the printing resolution of the 3D printer may be at least 6 µm, 8 µm or 10 µm. Preferably, the printing resolution is at least 12 µm, 14 µm or 16 µm.

The term "ink" can refer to the material dispensed by the 3D printer to perform the method according to the invention. Preferably, the ink is polymeric. The ink comprises a thermoplastic polymer, hot-melt glue and/or wax.

Preferred thermoplastic polymers may be selected from a group consisting of: poly-lactic acid (PLA), poly-caprolactone (PCL), Poly-glycolic acid (PGA), Poly(D,L-lactide-co-glycolide) (PLGA), Poly (D,L-lactide) (PLLA), polymethyl methacrylate (PMMA), chitosan, polyurethane, hydroxypropylmethylcellulose (HPMC), gelatine, or a combination thereof. The stents made using the method according to the invention may be made from any combination of the inks described herein.

The method preferably comprises heating the ink before it is expelled from the printer nozzle. By heating the ink, it can be dispensed more accurately by the printer nozzle. The ink may be heated by heating the nozzle. Preferably, the ink is heated to a temperature above the melting point or the glass transition temperature of the ink. Even more preferably, the method comprises heating the ink to a temperature that is 10° C., 5° C., 2° C. or 1° C. above the melting point/glass transition temperature of the ink before it is dispensed by the printer nozzle. The ink is dispensed in a semi-liquid state. The ink may be supplied to the dispensing head in the form of a flexible strand of solid material from an ink supply source. After the ink has been dispensed, the ink cools down, solidifies and bonds to the previously printed layer. Consequently, the stent is created by the depositing layer upon layer of printed ink.

The method preferably comprises moving the nozzle, preferably in x-, y- and/or z-planes, with respect to the position of the printed stent or a stage on which the stent is placed. For example, the printer nozzle may be attached to at least one moveable ink dispensing head, which may be moved in both horizontal and vertical directions with respect to the position of the printed stent or the stage on which the stent is placed.

Preferably, the method comprises detecting the temperature of the ink. The printer, and preferably the nozzle, may comprise a temperature sensor for detecting the temperature of the ink. Preferably, the method comprises controlling the temperature of the ink. The printer, and preferably the nozzle, may comprise a temperature controller operably connected to the temperature sensor for controlling the temperature of the ink. The advantage of having a temperature controller is that it ensures that the ink cools and solidifies in a consistent manner after it has been expelled from the nozzle, and this improves the efficiency of the printing process.

The method preferably comprises heating the ink before it is expelled from the nozzle. The nozzle may comprise a heater, which controls of the temperature of the ink as it is discharged, to ensure that the ink is in a fluid state slightly above its solidification temperature. The nozzle may comprise a means of stopping and starting the flow of the ink.

In another embodiment, the method according to the invention involves drop-on-demand (DoD) 3D printing. DoD involves making a partially complete stent support structure out of a support material during the stent printing process. The support structure may be made using a 3D printer. The support material and the ink may be deposited interchangeably. For example, the process may start with the support material being deposited on a stage, which is then followed by the ink, which is then followed by the support material, which is then followed by the ink, and so on. The support material used to create the stent support structure may be wax, glycol distearate, a fatty acid or a combination thereof. The wax may be hydroxylated wax, natural wax or synthetic wax. The hydroxylated wax may be 60 to 100% by weight, 70 to 90% by weight or 80 to 90% by weight. The natural wax may be 5 to 50% by weight, 10 to 40% by weight or 15 to 30% by weight. Preferably, the natural wax is 15 to 30% by weight when combined with synthetic wax, glycol distearate and a fatty acid. The synthetic wax may be 5 to 50% by weight, 10 to 40% by weight or 15 to 30% by weight. Preferably, the synthetic wax is 15 to 30% by weight when combined with natural wax, glycol distearate and a fatty acid. The glycol distearate may be 5 to 50% by weight, 10 to 40% by weight or 15 to 30% by weight. Preferably, the glycol distearate is 15 to 30% by weight when combined with synthetic wax, natural wax and a fatty acid. The fatty acid may be 5 to 50% by weight, 10 to 40% by weight or 15 to 30% by weight. Preferably, the fatty acid is 15 to 30% by weight when combined with synthetic wax, natural wax and a glycol distearate.

Preferably, the support material, is capable of being converted into a liquid state upon heating above its glass transition temperature/melting point, and solidifying upon cooling below its glass transition temperature/melting point. Preferably, the method comprises depositing the ink in or on the surface of the stent support structure. The ink is dispensed in the form of droplets. Ink is fed to individual nozzles as they move in along the x-, y- and/or z-axis of the stent.

The droplets of ink rapidly cool down and solidify once they have deposited in or on the support structure. The method may also comprising passing a milling head over the printed layer of the stent to ensure that it is of uniform thickness. Excess solidified ink may be vacuumed away as the milling head smoothens the stent. The excess solidified ink may be captured in a filter. The process is repeated until the entire stent has been formed. After the entire stent has been printed, the support structure may be removed by being dissolved in a solvent, which does not dissolve the ink of the stent, without the need for manual refining. Solvents used may be any appropriate solvent known in the art. Alternatively the wax may be removed by melting it using heat. The skilled person would appreciate that the support material will have a melting point/glass-transition temperature, which is significantly lower than that of the ink, in order to ensure that heating the wax does not melt or deform the stent. Preferably, the glass transition temperature or melting point of the support material may be least 2° C., 5° C., 10° C., 20° C., 50° C. or 100° C. above the glass transition temperature or melting point of the ink. Preferably and advantageously, the support material is a good thermal conductor so such that it reduces the amount of time required for the building material to solidify after it has been dispensed by absorbing heat, through conduction, from the ink.

A computer readable design may be a computer-aided design (CAD).

The inventors have shown that the method according to the invention may be used to create or print a drug-eluting stent. In one embodiment, therefore, the method may comprise applying a therapeutic agent or drug to a surface of the printed stent. The method may comprise applying the therapeutic agent to the surface of the stent by spraying. The method may comprise applying the therapeutic agent to the surface of the stent by dip-coating the stent in a bath of the therapeutic agent. Preferably, the method comprises applying the therapeutic agent to the surface of the stent by printing. Preferably, the biological activity of the therapeutic agent is not heat sensitive.

In another embodiment, the method may comprise contacting the ink with a therapeutic agent or drug to form a mixture which is then expelled through the nozzle to print the stent. The therapeutic agent may be mixed or homogenously distributed in the ink prior to printing. Preferably, the method comprises heating the mixture of the ink and the therapeutic agent, such that hot melt is extruded from the printer nozzle and used to create the stent. Preferably, the therapeutic agent is heat-resistant.

In a second aspect of the invention, there is provided a stent obtained or obtainable by the method according to the first aspect.

In one embodiment, the stent may be a bioabsorbable stent.

The term "bioabsorbable" can mean that it is capable of being absorbed into or degraded by living tissue. Bioabsorbable polymers, for example, may be degraded by living tissue and excreted or bioassimilated.

The ink used to print the bioabsorbable stent may be a thermoplastic polymer.

In another embodiment, the stent may be a drug-eluting stent. Drug-eluting stents are suitable for treating diseases or trauma that require therapeutic assistance while the vessel is being healed (i.e. during the healing window). The ink used to print the drug-eluting stent may be any ink according to the first aspect of the invention. The drug-eluting stent may be a stent comprising a therapeutically effective amount of a therapeutic agent.

In one embodiment, the therapeutic agent may be disposed on a surface of the stent. The therapeutic agent may be hydrophobic or hydrophilic. Preferably, the therapeutic agent disposed on the surface of the stent or struts is hydrophilic.

In another embodiment, the therapeutic agent may be distributed (preferably homogeneously) in the solidified ink of the stent. Therapeutic agents homogenously distributed in the solidified ink of the stent are slowly released, by diffusion, from the struts into the blood. It will be appreciated that solidified ink forming the struts can be used to control the rate of diffusion of a therapeutic agent, which is homogenously distributed in the solidified ink of the stent, out into the blood. More complex and tightly packed inks are suitable for creating drug-eluting stents with slow release properties. Preferably, the ink of the drug-eluting stent comprises a polymer, which permits slow-release of the therapeutic agent out of the ink of the stent. Polymers that permit slow-release of therapeutic agents may be poly-lactic acid (PLA), poly-caprolcatone (PCL), Poly-glycolic acid (PGA), Poly(D,L-lactide-co-glycolide) (PLGA), Poly (D,L-lactide) (PLLA), polymethyl methacrylate (PMMA), chitosan, polyurethane, hydroxypropylmethylcellulose (HPMC), gelatine, or a combination thereof. This is achieved by mixing the therapeutic agent with the ink prior to printing. The therapeutic agent mixed with the ink may be heat-resistant, such that it does not lose any therapeutic activity in response to being heated.

The therapeutic agent may be hydrophobic or hydrophilic. A hydrophobic therapeutic agent may be, for example, warfarin, paclitaxel, sirolimus, simvastatin, everolimus, zotarolimus, biolimus or combinations thereof. A hydrophilic therapeutic agent may be, for example, a polypeptide, a protein or heparin.

Advantageously, the drug-eluting stents of this embodiment may be used to deliver a high concentration of a hydrophobic therapeutic agent to a specific site within the vasculature. This is advantageous because hydrophobic therapeutic agents are insoluble in blood. Consequently, high concentrations of a hydrophobic therapeutic agent must be administered systemically in order to achieve a therapeutically effective concentration of the hydrophobic therapeutic agent at the desired specific location in the vasculature. Preferably, the therapeutic agent homogenously distributed in the solidified ink of the stent is hydrophobic.

In another embodiment, the drug-eluting stent may comprise two therapeutic agents, a first agent on the surface of the struts and a second agent distributed in the ink of the stent.

The therapeutic agent may be, but is not limited to, an anti-inflammatory agent, anticoagulant, antiplatelet drug, immunosuppressant drug, antimitotic drug, glucocorticoid, aspirin, ACE inhibitor, paclitaxel, dexamethasone, Zoatarolimus, Biolimus Estradiol, flavonoid, a polysaccharide, glucose, an amino acid or a combination thereof. Heat-resistant therapeutic agents may be, for example, paclitaxel, sirolimus or dexamathasone.

The therapeutic agent may be in the form of a powder, liquid, ointment, cream, gel, hydrogel, micellar solution, liposome suspension or any other suitable form that may be sprayed or extruded on to the exterior surface of the struts and/or homogenously distributed in the ink of the struts.

A "therapeutically effective amount" of the therapeutic agent is any amount which, when administered to a subject, is the amount of medicament or drug that is needed to treat stenosis or produce the desired effect.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

It will be appreciated that in order for a stent to be effective, it must exhibit sufficient radial strength to counteract the stenotic vessel. However, a stent must also be flexible enough so that it is capable of expanding in response to a balloon angioplasty during surgery.

The inventors found that these properties can be achieved with careful design of the stent and by the use of an ink that has an ideal tensile strength. Preferably, the ink has a tensile strength above 10 megapascal (MPa), 15 MPa or 20 MPa. Preferably, the ink has a tensile strength below 500 MPa, 375 MPa or 250 MPa. The ink may have a tensile strength of 10 to 500 MPa, 15 to 375 MPa or 20 to 250 MPa. Preferably, the ink has a tensile strength of 50 to 120 MPa.

The inventors found that properties such as the width and thickness of the struts have a significant impact on the ability to print stents according to the invention. If the width or thickness of the strut is too thick, then the struts of the stent become stacked together. If the width or thickness of the strut is too thin, then the struts of the stent collapse. Consequently, the thickness of struts of the stent according to the invention may be at least 80 µm, 100 µm or 150 µm. Preferably, the thickness of the struts is at least 200 µm, 250 µm or 300 µm. The thickness of the struts of the stent may be at most 650 µm, 600 µm or 550 µm. Preferably, the thickness of the struts is at most 500, 450 µm or 400 µm. It will be envisaged that any combination of the upper and lower values of the strut thickness may be envisaged. For example, the thickness of the struts may be 80 µm to 650 µm, 100 to 600 µm or 150 to 550 µm. Preferably, the thickness of the struts is 200 to 500 µm, 250 to 450 µm or 300 to 400 µm.

The width of the struts of the stent according to the invention may be at least 80 µm, 100 µm or 150 µm. Preferably, the width of the struts is at least 200 µm, 250 µm or 300 µm. The width of the struts may be at most 650 µm, 600 µm or 550 µm. Preferably, the width of the struts is at most 500 µm, 450 µm or 400 µm. It will be envisaged that any combination of the upper and lower values of the strut width may be envisaged. For example, the width of the struts may be 80 µm to 650 µm, 100 to 600 µm or 150 to 550 µm. Preferably, the width of the struts is 200 to 500 µm, 250 to 450 µm or 300 to 400 µm.

The inventors also found that solidified ink that exhibits large elongation at break properties can be used to generate stents with sufficient tensile strength. Preferably, the ink, when solidified, has a radial expansion at break percentage of 10 to 1000%, 25 to 750% or 50 to 500%. Preferably, the ink has an axial elongation at break percentage of 5 to 500%, 10 to 375% or 20 to 200%.

In order to successfully counteract stenosis, a stent must contact the internal surface area of the section of vasculature in which it is located. This is referred to herein as vascular coverage. The vascular coverage of the stent may be 5 to 60%, 10 to 50% or 10 to 40%. Preferably, the vascular coverage of the stent is 10 to 25%.

Stents according to the invention may be at least 2 mm, 5 mm or 10 mm in length. In another embodiment, the stent may be at most 50 mm, 40 mm or 30 mm in length. In another embodiment, the stent may be 2 to 50 mm, 5 to 40 mm or 10 to 30 mm in length.

Stents according to the invention may be at least 1 mm, 1.5 mm or 2 mm in diameter. In another embodiment, the stent may be at most 15 mm, 10 mm or 5 mm in diameter. In another embodiment, the stent may be 1 to 15 mm, 1.5 to 10 mm or 2 to 5 mm in diameter.

It will be appreciated that the method according to the invention may be used to create a wide variety of stents, which may be used to treat a wide variety of diseases. For example, the stent according to the invention may be a vascular stent, an abdominal stent, a urethral stents, a prostatic stent or an oesophageal stent.

In a third aspect, there is provided the stent according to the second aspect, for use in treating a vascular disease.

The vascular disease may be stenosis, restenosis, thrombosis, hypertension, hemophilia, angioedema, hyperlipidemia, vasculitis, peripheral vascular disease, an aneurysm or an intracranial aneurysm.

In a fourth aspect, there is provided a method of treating a vascular disease in a subject in need of such treatment, the method comprising fitting the stent according to the second aspect into a blood vessel of the subject.

The vascular disease may be stenosis, restenosis, thrombosis, hypertension, hemophilia, angioedema, hyperlipidemia, vasculitis, peripheral vascular disease, an aneurysm or an intracranial aneurysm.

The blood vessel may be an artery, an arteriole, a vein or a venule.

In a fifth aspect, there is provided an electric signal carrying computer-executable instructions adapted to cause a 3D printer to print a stent.

In a sixth aspect, there is provided a computer program comprising computer-executable instructions adapted to cause a 3D printer to print a stent.

In a seventh aspect, there is provided a computer readable medium storing computer-executable instructions adapted to cause a 3D printer to print a stent.

A computer readable medium may be a computer-aided design (CAD) file.

The stent printed in accordance with the fifth to seventh aspects may be as defined in the second aspect, i.e. using the method of the first aspect.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which.

EXAMPLES

Figure 1:
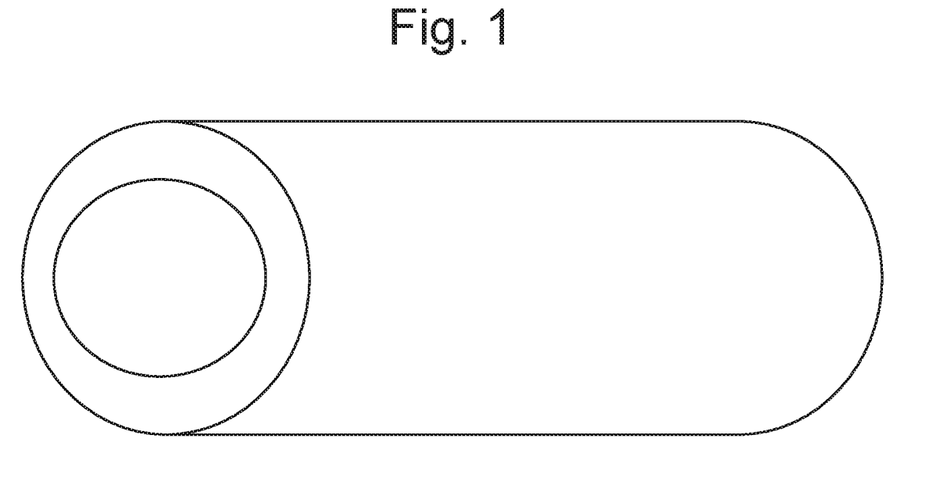
FIG. 1 is a hollow tube/cylinder from which a prior art stent is created.
Figure 2:
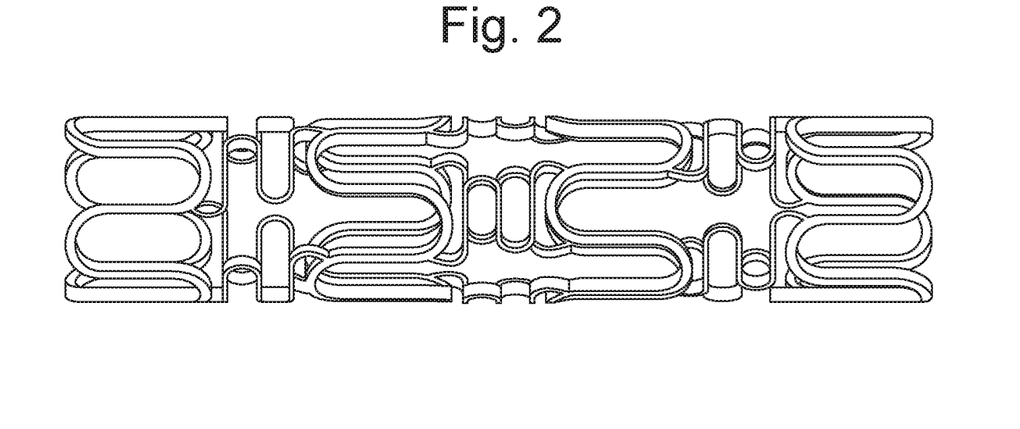
FIG. 2 is a computer-aided design of a first embodiment of a prior art stent.
Figure 3:
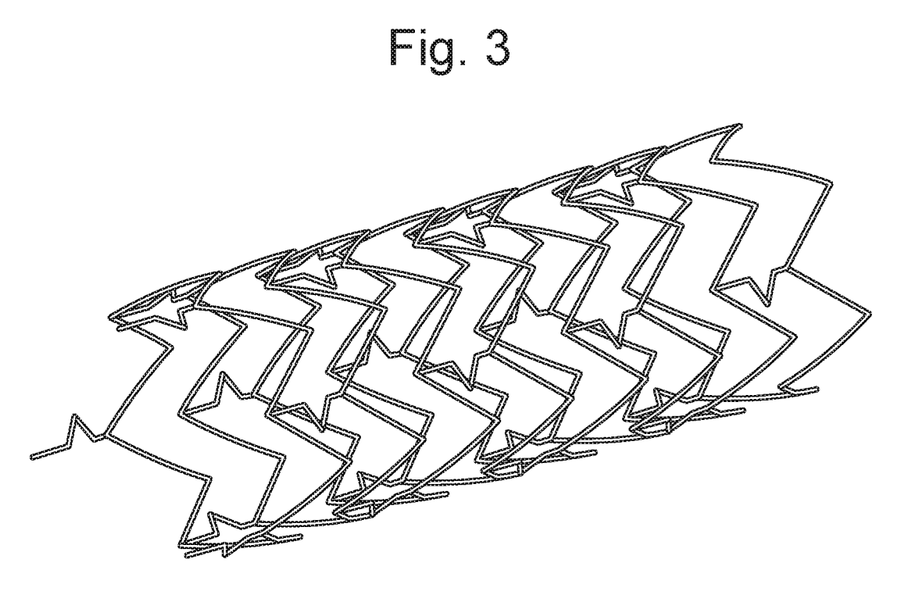
FIG. 3 is a computer-aided design of a second embodiment of a prior art stent.
Figure 4:
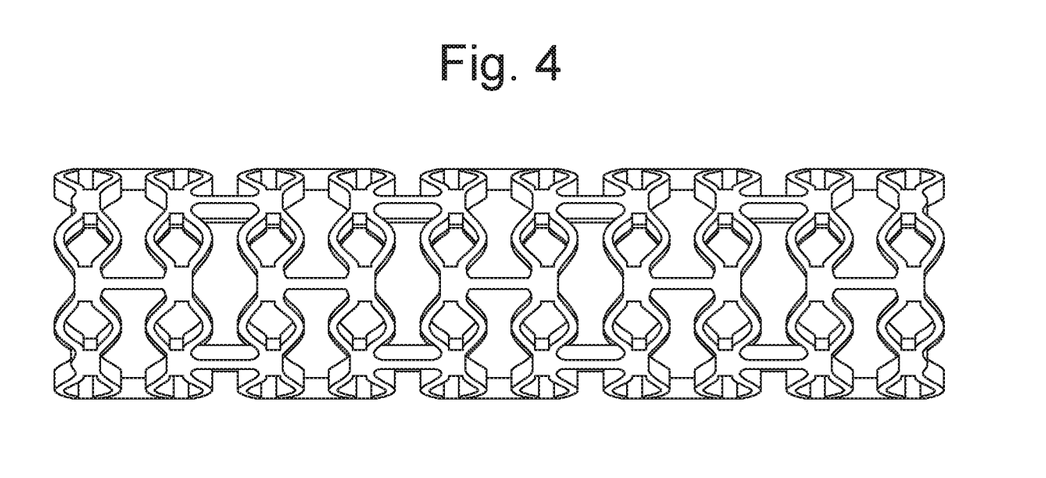
FIG. 4 is a computer-aided design of a third embodiment of a prior art stent.

FIG. 1 shows a hollow metallic cylinder, which may be converted into a prior art stent using known laser cutting technology. A laser cutter is used to cut and remove material from the wall of the cylinder, such that the cylinder is converted into a mesh tube or stent. The diameter of the cylinder must be small enough so that once it has been converted into a stent, it can be introduced into the lumen of the relevant blood vessel of a subject needing therapy. Referring to FIG. 2, there is shown a computer-aided design (CAD) of a prior art stent, which has been created from a metallic cylinder such as the one shown in FIG. 1. FIGS. 3 and 4 are CADs of alternative embodiments of prior art stents. Each stent comprises interconnected struts of varying lengths, shapes and thickness.

Example 1

CADs of Stents According to the Invention

Figure 11:
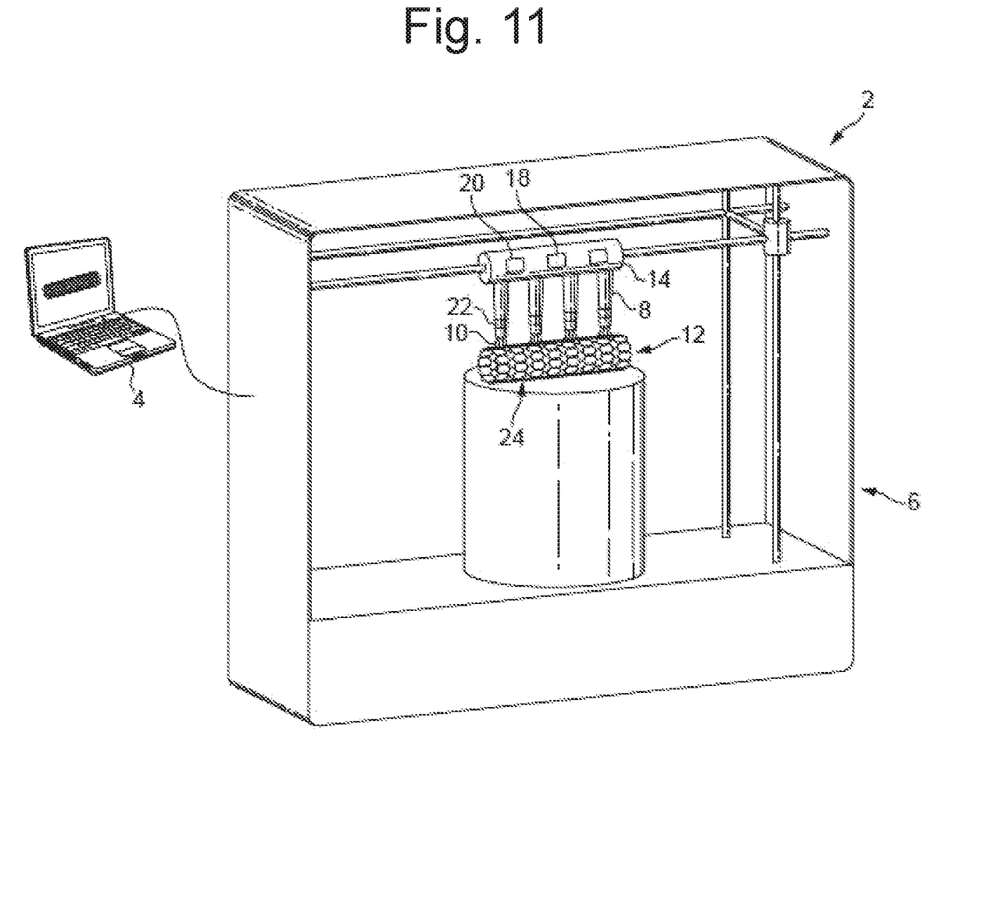
FIG. 11 is a schematic of an embodiment of an apparatus used to print stents according to the invention.
Figure 12:
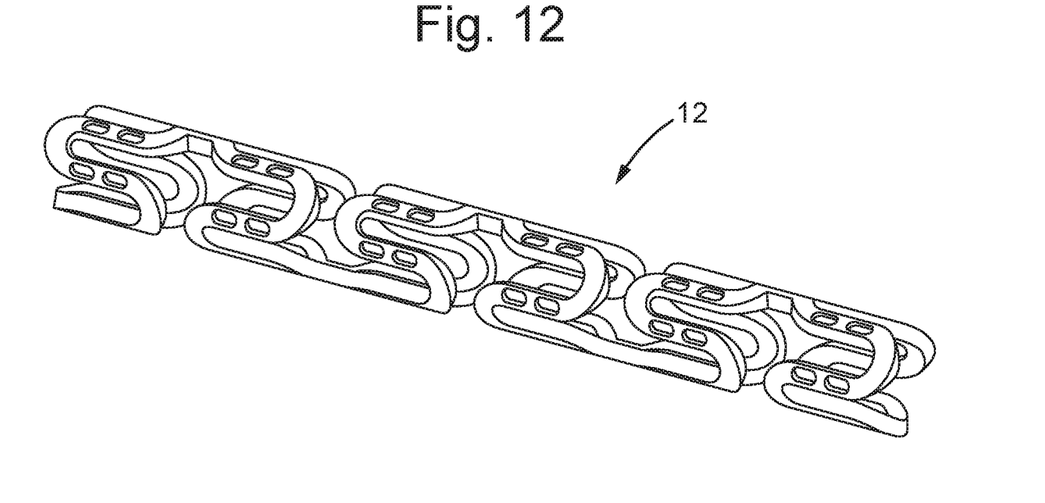
FIG. 12 is a computer-aided design of a third embodiment of a stent created by the method and apparatus according to the invention.
Figure 13:
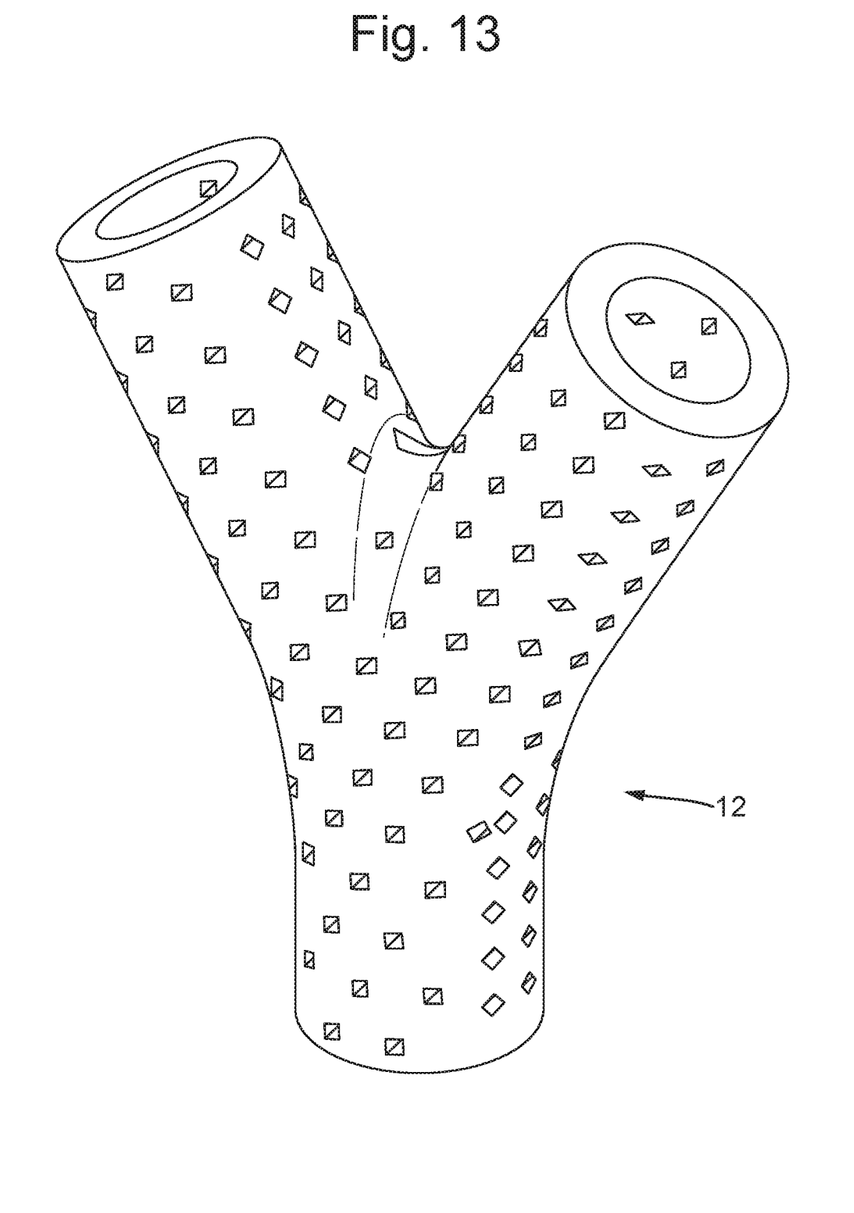
FIG. 13 is a computer-aided design of a fourth embodiment of a stent created by the method and apparatus according to the invention.

FIGS. 5, 6, 12 and 13 are CADs of stents 12 that have been printed from a polymer such as polylactic acid (PLA) using the method according to the invention and apparatus 2 shown in FIG. 11, as described below.

Example 2

Apparatus for Creating the Stent

Referring to Figure ii, there is shown an apparatus 2 for producing the stent 12 using 3D printing. Each stent 12 was designed using the CAD software, SolidWorks, and then uploaded in the form of an .stl file on to a control computer 4. The control computer 4 is connected to a Fortus 900 3D printer 6 which includes two dispensing heads 14, each having a nozzle 8 responsible for dispensing the ink 10 used to create the stent 12. Each nozzle has an aperture of 100 to 300 µm in diameter through which the polymeric ink 10 is ejected.

After the .stl file had been uploaded onto the control computer 4, the computer 4 slices the schematic representation of the stent 12 into a plurality of layers and simultaneously directs the x-y movement of the nozzles 8 and the z-movement of a stage 26 on which the resultant stent 12 is supported in accordance with the CAD representation in order to selectively dispense the ink material 10 at the appropriate areas to form the 3D stent 12. PCL is supplied as the polymeric ink 10 to the dispensing heads 14 of the printer 6 in the form of a flexible strand of heated material. Once melted at a temperature of 150° C., the PCL is dispensed by the printer nozzles 8, and it cools down and creates a first layer of printed PCL, which is supported on the stage 26. As more heated PCL is ejected from the heads 14, the next layer binds to the previous layer of printed PCL. The thickness of the layers of PCL is about 300 µm.

The printing apparatus 2 also comprises a temperature controller 18, which is responsive to temperature sensors 20 disposed on the dispensing head 14 of the printing apparatus 2. The temperature controller 18 finely adjusts the temperature of the PCL such that it is approximately 1° C. above the temperature at which PCL 10 solidifies so that it solidifies just after it has been deposited on the previous layer of ink. This improves the precision with which the nozzle 8 can dispense the PCL used to create the stent 12. A supplemental heater 22 disposed on the nozzle tip 8 responsive to the temperature controller 18 provides accurate control of the temperature of the ink material 10 as it is discharged, to ensure that it is in a fluid state slightly above its solidification temperature 150° C.

Alternatively, the apparatus may be used to perform DoD 3D printing. A partially complete wax mould of the stent 12, which acts as a support structure, is filled or coated in microdroplets of PCL. The wax may, for example, be 3Z Support, from Solidscape. The PCL is dispensed in the form of microdroplets at a temperature ranging from 50° C. to 70° C. As the PCL cools, it solidifies on the wax mould to form the stent 12. A milling head is then passed over the printed stent in order to ensure that it is of uniform thickness. After the stent has been completed the wax mould is then removed by melting it.

Example 3

Stents

Figure 6:
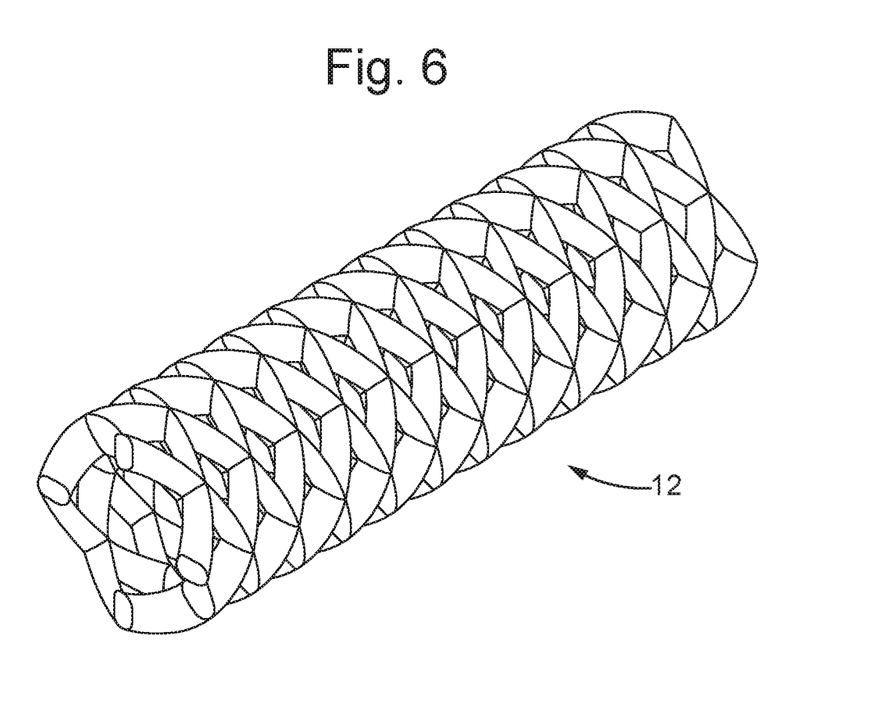
FIG. 6 is a computer-aided design of a second embodiment of a stent created by the method and apparatus according to the invention.
Figure 7:
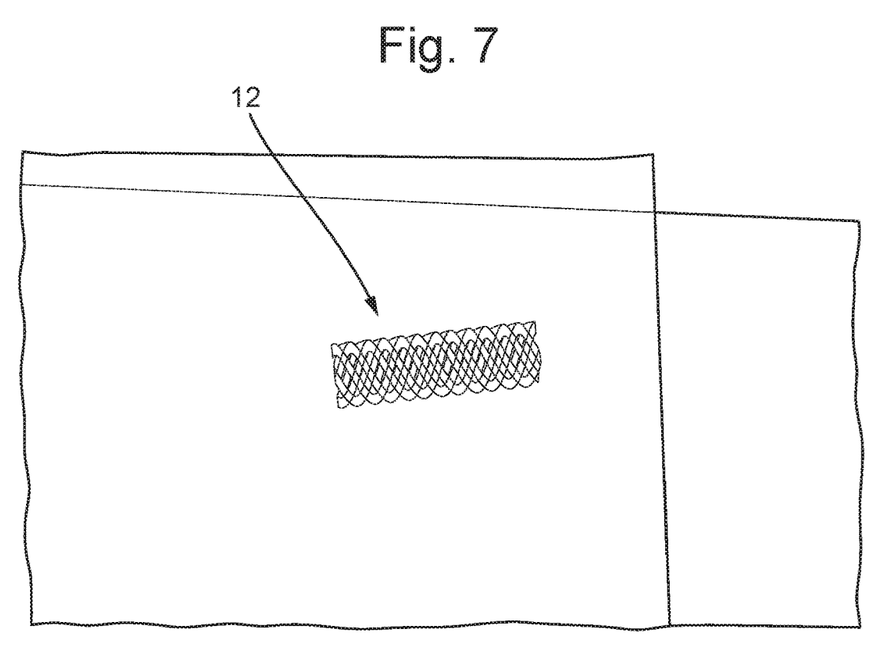
FIGS. 7 to 8 are pictures of a drug-eluting stent created by the method according to the invention, which are based on the embodiment of FIG. 6.
Figure 8:
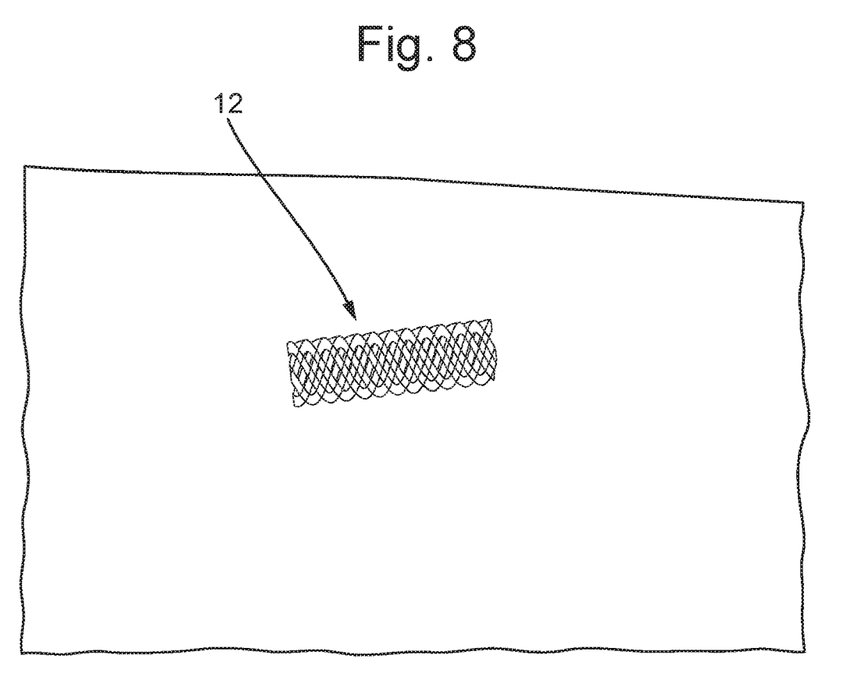

FIGS. 7 to 8 show a stent 12 that has been made, based on the CAD of FIG. 6, using the 3D printer 6 connected to computer 4 with the SolidWorks program. The struts 24 of the stent 12 are 300 µm thick and have a width of 340 µm. The stent 12 covers approximately 10 to 25% of the internal surface area of the section vasculature in which it is located.

Figure 5:
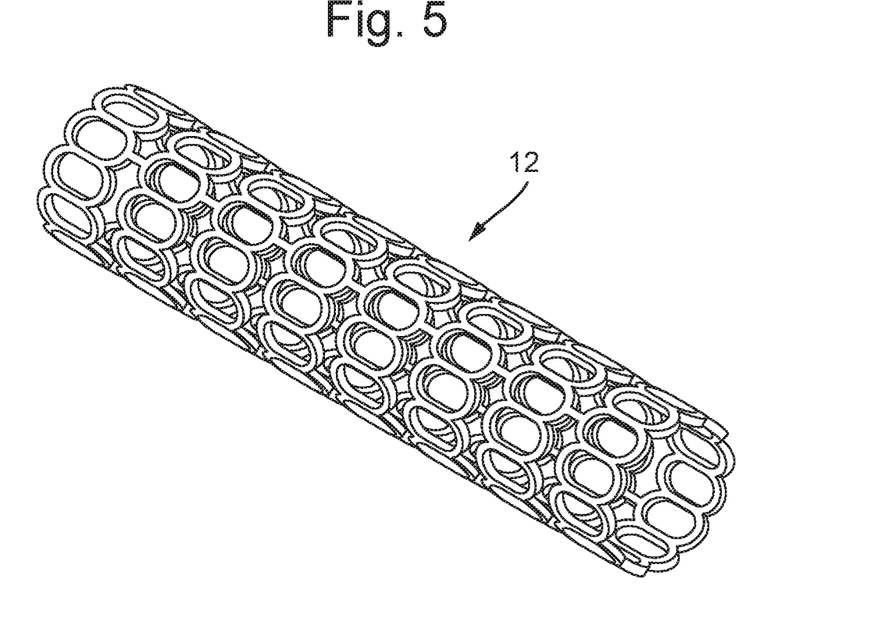
FIG. 5 is a computer-aided design of a first embodiment of a stent created by the method and apparatus according to the invention.
Figure 9:
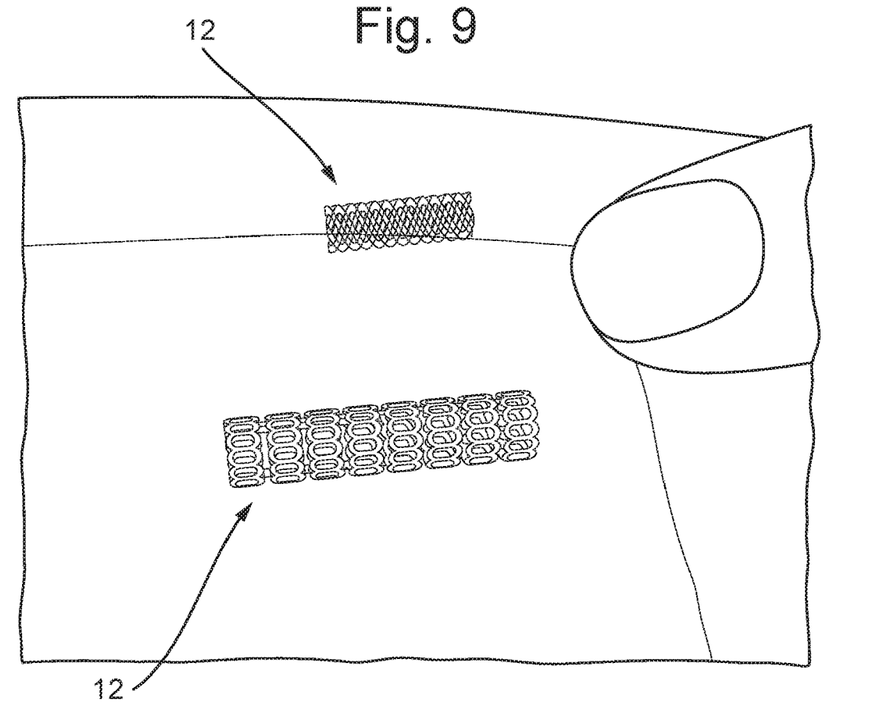
FIG. 9 is a picture of a drug-eluting stent created by the method according to the invention, which is based upon the embodiment of FIGS. 5 and 6.

Similarly, FIG. 9 shows two stents 12 that have been made, based on the CADs of FIGS. 5 and 6, using the method according to the invention. These stents 12 have been created by building successive layers of PLA ink material on top of each other (i.e. additive manufacturing). They have been made from PLA, which is bioabsorbable polymer. PLA is a biocompatible material that is less likely to cause any of the problems associated with prior art stents.

Example 4

Drug-eluting Stents

Figure 10:
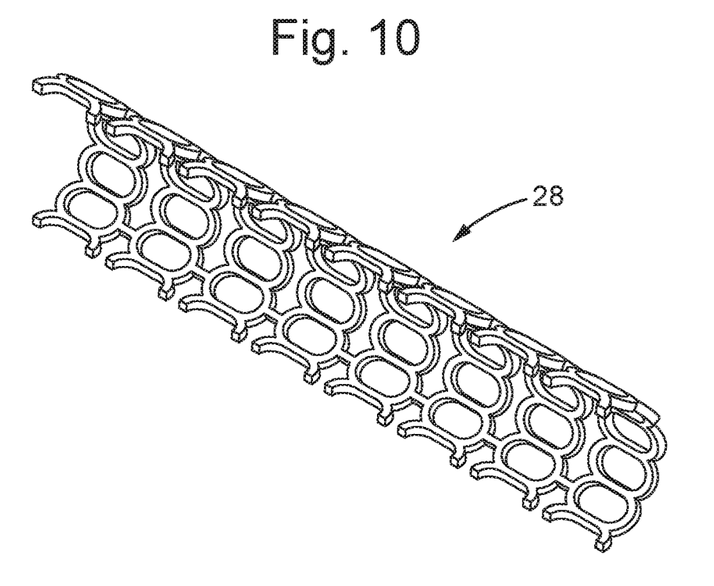
FIG. 10 is a computer-aided design of a cross-section of a drug-eluting stent according to the invention.

The apparatus and method described above has also been used to create a drug-eluting stent 28, as shown in FIG. 10. This embodiment of the stent 28 is rendered drug-eluting by two different methods.

In the first approach, the drug or therapeutic agent and the PLA polymer are simultaneously extruded (i.e. hot melt extrusion) to produce an ink strand 10 (1.7 mm) which is ejected from the nozzles 8. The drug is homogeneously distributed within the structure of the polymeric stent 12 itself, and this approach applies to heat-resistant drugs (e.g. Paclitaxel). Hence, the drug surrounds the polymeric ink, which has been used to create the struts 24 of the stent 12. This embodiment is capable of temporarily storing a drug/composition that can slowly be eluted through the walls of the struts 12 into the blood vessel in which the stent 12 is inserted.

In a second approach to make the drug-eluting embodiment of the stent 12, the PLA polymer ink 10 is extruded without the drug, and the stent 12 is printed following the same process as described in Examples 2 and 3. The drug is then coated on the stent's outer surface by spraying it onto the surface of the stent using any device which can generate microdroplets and can be used for fine spray applications. These devices can based on inkjet printing technology (piezoelectric, thermal, electrostatic), ultrasonic spray technology, air brush technology. Hydrophobic drugs such as, sirolimus and paclitaxel, may need to be dissolved in ethanol prior to spraying, ink jetting from an organic solution such as dissolved in ethanol. This approach applies to heat sensitive drugs (e.g. Biolimus or Zotarolimus). In this embodiment, the drug is located primarily on the outer layers of the stent 12 where it is expected to have a faster release rate.

SUMMARY

Advantages of the Method and Apparatus 2 of the Invention Reside in:
- the diameter of the aperture of the printer nozzle 8 through which the ink 10 is ejected. Each nozzle has an aperture of 100 to 300 µm in diameter;
- the thickness of each printed layer. The thickness is 6 to 32 µm;
- the thickness of the struts 24 of the stent 12 is about 300 to 400 µm;
- the width of the struts of the stent 12 is about 300 to 400 µm;
- the length of the stent 12 is about 2 to 50 mm;
- the vascular coverage of the stent 12 is about 10 to 25%;
- the ink 10 used to create the stent 12 and its mechanical properties, e.g. PLA;
- the temperature at which the ink 10 is dispensed or printed, i.e. 1° C. above the melting point/glass transition temperature of the ink; and the 3D printer software used (i.e. SolidWorks) because they provide variable printer resolution.

The invention claimed is:

1. A method of manufacturing a stent using a three dimensional (3D) printer, the method comprising:
   (i) installing a computer-readable design of a stent on a computer, which is operably connected to a 3D printer comprising a nozzle and a stage; and
   (ii) instructing the 3D printer to print the design of the stent, such that
      a) non-metallic ink comprising a thermoplastic polymer is heated to a temperature at least 1° C. above the melting point/glass transition temperature of the ink, and is then expelled from the nozzle onto the stage to form a first layer of printed material, and consequently depositing layer upon layer of printed ink to thereby form the stent, or
      (b) a support material is expelled from the nozzle onto the stage to form a first layer, and then non-metallic ink comprising a thermoplastic polymer is heated to a temperature at least 1° C. above the melting point/glass transition temperature of the ink, and is then expelled from the nozzle onto the first layer to form a second layer, and the support material and the non-metallic ink are then expelled alternately to form alternate layers, and thereby form the stent.

2. A method according to claim 1, wherein the diameter of the printer nozzle outlet aperture is at least 10 μm, 25 μm, 50 μm, 75 μm, 85 μm or 100 μm, or wherein the diameter of the printer nozzle outlet aperture is less than 600 μm, 500 μm, 450 μm, 400 μm, 350 μm or 300 μm.

3. A method according to claim 1, wherein the printing resolution of the 3D printer is at least 6 μm, 8 μm, 10 μm, 12 μm, 14 μm or 16 μm.

4. A method according to claim 1, wherein the method comprises heating the ink to a temperature that is 10° C., 5° C., or 2° C. above the melting point/glass transition temperature of the ink before it is dispensed by the printer nozzle.

5. A method according to claim 1, wherein the ink is dispensed in a semi-liquid state or in the form of droplets.

6. A method according to claim 1, wherein the method comprises depositing the ink in or on the surface of a stent support structure.

7. A method according to claim 5, wherein the method comprises passing a milling head over the printed layer of the stent to ensure that it is of uniform thickness.

8. A method according to claim 1, wherein the computer-readable design is a computer-aided design (CAD).

9. A method according to claim 1, wherein the method comprises applying a therapeutic agent to the surface of the stent by spraying or by printing.

10. A method according to claim 1, wherein the method comprises contacting the ink with a therapeutic agent or drug to form a mixture which is then expelled through the nozzle to print the stent.

11. A method according to claim 10, wherein the method comprises heating the mixture of the ink and the therapeutic agent, such that hot melt is extruded from the printer nozzle and used to create the stent.

12. A stent obtained or obtainable by the method according to claim 1, wherein the ink has a tensile strength above 10 MPa.

13. A stent according to claim 12, wherein the stent is a bioabsorbable stent or a drug-eluting stent comprising a therapeutically effective amount of a therapeutic agent.

14. A stent according to claim 13, wherein the therapeutic agent is hydrophobic or hydrophilic or wherein the therapeutic agent is distributed in solidified ink of the stent.

15. A stent according to claim 12, wherein the ink has a tensile strength above 15 megapascal (MPa) or 20 MPa, or a tensile strength below 500 MPa, 375 MPa or 250 MPa.

16. A stent according to claim 12, wherein the thickness of struts of the stent is at least 80 μm, 100 μm or 150 μm, or at most 650 μm, 600 μm or 550 μm.

17. A stent according to claim 12, wherein the vascular coverage of the stent is 5 to 60%, 10 to 50% or 10 to 40%.

18. A method of treating a vascular disease in a subject in need of such treatment, the method comprising fitting the stent according to claim 12 into a blood vessel of the subject.

19. A method according to claim 18 wherein the vascular disease is stenosis, restenosis, thrombosis, hypertension, hemophilia, angioedema, hyperlipidemia, vasculitis, peripheral vascular disease, an aneurysm or an intracranial aneurysm.

20. A method according to claim 1, wherein the thermoplastic polymer is selected from the group consisting of: poly-lactic acid (PLA), poly-caprolcatone (PCL), poly-glycolic acid (PGA), poly(D,L-lactide-co-glycolide) (PLGA), poly (D,L-lactide) (PLLA), polymethyl methacrylate (PMMA), chitosan, polyurethane, hydroxypropylmethylcellulose (HPMC), gelatine, and combinations thereof.

21. A method according to claim 1, wherein the stage comprises a substantially flat surface.

* * * * *